United States Patent [19]

Kvanta

[11] 4,210,673

[45] Jul. 1, 1980

[54] PROCESS FOR FERMENTATION OF GREEN FODDER

[75] Inventor: Endre Kvanta, Angelholm, Sweden

[73] Assignee: AB Medipharm, Sweden

[21] Appl. No.: 877,983

[22] Filed: Feb. 15, 1978

[30] Foreign Application Priority Data

Feb. 16, 1977 [SE] Sweden .................................. 7701687

[51] Int. Cl.² .............................................. A23K 3/02
[52] U.S. Cl. ........................................ 426/53; 426/54; 426/807
[58] Field of Search ...................... 426/52, 53, 54, 807; 195/96

[56] References Cited

U.S. PATENT DOCUMENTS

| | | | |
|---|---|---|---|
| 1,257,754 | 2/1918 | Sonderegger et al. ................ | 426/53 |
| 2,890,956 | 6/1959 | Bonda .................................... | 426/54 |
| 3,459,554 | 8/1969 | Hashimoto ......................... | 426/53 X |
| 3,677,897 | 7/1972 | Jeffreys .............................. | 426/54 X |

OTHER PUBLICATIONS

Bergey's Manual of Determinative Bacteriology 8th Edition Williams & Wilkens Company Baltimore pp. 490-495 & 504-506.

*Primary Examiner*—R. B. Penland
*Attorney, Agent, or Firm*—Ostrolenk, Faber, Gerb & Soffen

[57] ABSTRACT

Green fodder is fermented with a lactic acid producing *Streptococcus faecium* producing a metabiolite having anti *E-coli* activity.

6 Claims, No Drawings

PROCESS FOR FERMENTATION OF GREEN FODDER

BACKGROUND OF THE INVENTION

This invention relates to a process for the manufacture of pressed fodder controlled by lactic acid fermentation and is especially related to a process for fermentation of green fodder in a silo or similar apparatus for preservation purposes. The expression "green fodder" means green plants or plant parts such as root crops tops, after crop or pasture grass, and "pressed fodder" means such green fodder which has been pressed together in a silo or similar apparatus, usually by its own weight.

It is known that preservation of green fodder can be accomplished by "sourmaking", which can either be by self-fermentation or by the addition of a suitable acid. The acid preserved green fodder can be used for feed, especially for cattle.

It is also known that sourmaking in principle can be effected in two different ways. According to one, the green fodder is collected in silos or the like where self-fermentation can take place during generation of, among other things, lactic acid. In fermentation, nondesirable break-down-products such as butyric acid are also often formed. These non-desirable by-products cause the quality of the pressed fodder to deteriorate to a high extent. Another disadvantage in self-fermentation is the fact that the protein-value of the pressed fodder often decreases, generally up to 70%. These disadvantages result in heavy losses when the fodder is used in connection with the production of cattle and milk. The self-fermentation-method is, in general, very uncertain and often leads to a total putrefaction of the green fodder, especially due to influence of temperature. This method is very seldom used today.

The most common method used when manufacturing pressed fodder involves the collection of green fodder in a silo or the like and feeding a suitable acid, i.e. hydrochloric acid or a mixture of different acids, to the green fodder. Besides mineral acids, organic acids such as formic and propionic acid can be used. The pH in the green fodder treated in this way is so low so that putrefaction bacterias cannot develop. At the same time, it is possible to preserve the nutritional quality of the fodder. Before using the sourmade green fodder, i.e., the so called sour fodder, the acid or acids are often neutralized by a suitable base, e.g. lime. The disadvantage of this type of treatment is that substances having small or no nutritional content at all are supplied. The handling of corrosive acids also involves considerable inconvenience and requires special installations.

According to the present invention, the above mentioned disadvantages are eliminated by a controlled lactic acid fermentation.

This invention thus relates to a process for fermentation of green fodder in a silo or the like, where the green fodder is compressed to a press fodder. The method according to the present invention is characterized in that to the green fodder is supplied a culture of a bacteria organism producing lactic acid, belonging to Streptococcus, that the fermentation is effected in the presence of a nitrogen source, a source of carbohydrates which can break down the essential growth factors at a temperature of at least 15° C. and in other respects under such conditions that the final grade of lactic acid in the press fodder is at least 2%.

In industrial production of lactic acid, on pure lactic acid, as well as on manufacture of different dairy products and other fermented provisions, organisms belonging to the family Lactobacillaceae are often used. In this connection, different types of Lactobacillus and types of Streptococcus included in the so called lactic acid group are most often used.

According to the present invention, organisms belonging to the group Enterococcus and especially *Streptococcus faecium* are used for the production of lactic acid. The Bergeys Manual of 1957 does not identify *Str. faecium* as an independent strain. Later literature (Whittenbury, Deibel etc. 1964) separates the group D-Streptococcus, the so called Enterococcus, in such a way that *Str. faecium* is included as an independent type. Further, it is stated that the type consists of a number of strains which can differ from each other regarding simple biochemical and immunological qualities. Simplified, this means that *Str. faecium* is a middle group between *Str. durans* and *Str. faecalis*. The differences from *Str. faecalis* are important: strains from faecium require folic acid as an essential grown factor which is not the case with faecalis.

Strains from *Str. faecium* have been isolated from the intestinal flora of human beings, pig, cattle, sheep and poultry. *Str. faecium* belongs to the natural intestinal flora in these organisms.

The *Str. faecium* organisms are homo-fermentative, i.e. only producing lactic acid when breaking down utilizable carbohydrates. Types that do not produce soluble hemolysines are regarded as complete apatogenic, and higher organisms' tolerance to high percentage of *Str. faecium* is very good. No serious negative effects are known in the peroral supply of these.

Str. faecium can use most of the mono- and disaccarides as a carbon source. Thus, 2 moles lactic acid are made from 1 mole monosaccarides (Glucose). The final pH in non-buffered cultures is between 3.6 and 4.0.

In treating green fodder to produce sour fodder fermentatively, the most suitable method is to use types belonging to Lactobacillus. It is known that different types of Lactobacillus can be used to stabilize the intestinal flora in domestic animals. It would consequently be natural to utilize Lactobacillus for the production of lactic acid and thereby achieve several advantages at the same time, viz. preservation of the fodder and a delivery of Lactobacillus with the ensilage to the animals. Such a delivery of different so called lactogenic organisms (Lactobacillus and Streptococcus) for preventive or therapeutical purposes is, in general, called Lactobacillus therapy.

It is known that organisms used in Lactobacillus therapy by production of lactic acid can prevent or decrease the growth of microorganisms, which commonly are called proteolytic. Such organisms are responsible for putrefaction in nature while others are patogenic if they are allowed to grow in the intestinal channel.

In the same way as the composition of the intestinal flora can be influenced by supporting the growth of the lactogenic bacterias (Bullen Willis 1971), the growth of such organisms in, for instance, treatment of press fodder can prevent and break, respectively, the growth and metabolism of proteolytic organisms. The first reason for the antagonistical effect seems to be the ability of the lactogenes to produce lactic acid. As an example of the selective rate of the lactic acid environment is the fact that there has been measured an average pH value of 5.1 in a lactobacillus-dominant intestinal microflora, while in a so-called coli-dominant intestinal flora, the corresponding value was 6.5. At the same time, coliformic bacterias and enterococus have been able to grow while in the former case only Lactobacillus grows. In the coli-dominant intestinal flora, there has also been found types of Chlostridium, Bacterocides, Proteus and Pseudomonas. Several of these types are proteolytic and pathogenic. The relations are similar in most of the biological materials having a spontaneous non-controlled fermentation.

One way to prevent a non-controlled fermentation of pressed fodder should be to supply a relevant quantity of a suitable strain of Lactobacillus at which time also the specific demands regarding nutrition supply and temperature for a rapid lactic acid production should be assured. Practical tests have, however, shown that it is difficult to achieve a high lactic acid production with justifyable quantities of some Lactobacillus type, i.e. Lacidopohylus. The reason for this seems to be the long generation time of the Lactobacillus, i.e. the slow growth speed.

It has been mentioned before that the concentration of lactic acid in a fermented product is of essential importance to preservation. Consequently, there is a quantitative connection between ability to have preservation effect and the ability to produce lactic acid in lactogenic organisms. There seems to be no significant differences between the different lactogenic organisms. It has been found necessary that the lactic acid concentration reach a certain threshold value to prevent growth of nondesirable microorganisms. When treating the pressed fodder with lactic acid producing bacterias, the result is to a very high extent influenced by how quick the threshold value of the lactic acid concentration is reached. During too slow growth and too slow lactic acid production, the putrefaction can reach such proportions by the growth of proteolytic microorganisms that the result will be unacceptable even if further growth of these organisms successively is stopped.

According to a preferred embodiment of the process of the invention, a culture of a lactic acid producing bacteria organism belonging to Streptococcus having a generation time (half-life) of 30 min. maximum and which is homofermentative is used. The advantage thereby achieved is that the above mentioned threshold value can be reached quickly, and also that only lactic acid is produced.

In connection with the invention, it has found that Streptococcus faecium is especially suitable for a rapid lactic acid production and that the threshold value of the lactic acid concentration can quickly be reached when treating the green fodder for the purpose to produce pressed fodder (ensilage).

Besides the ability to produce lactic acid and having a biostatic effect by a pH-decrease, *Str. faecium* seems to be able to also produce soluble metabolite which directly or indirectly has a bacteriostatic/bacteriocidal effect.

By investigation, it has found that the cell-free medium from *Str. faecium* cultures has a strong anti-E-coli-activity (bacteriostatic effect). Furthermore, it has found that several other strains of lactogenic Streptococcus and Lactobacillus which produce quantatively comparable quantities of lactic acid are missing anti-E-coli-activity in cell free medium. The explanation of the bacteriological effect of the cell free medium could either be the fact that the medium contains some bacteriostatic/bacteriocidal substance such as 2-deoxi-D-glucose, or the fact that *Str. faecium* produces a substance which functions as an activator of the so called Lactoperoxidase system, such as hydrogen peroxide.

This principle works in such a way that the hydrogen peroxide which is produced in small quantities of several bacteria types activates lactoperoxidas which is in most bacteriological materials. Lactoperoxidas transforms, in its turn, SCN-ions, which are commonly found in biological material, to an intermediar which is strongly bactericidal.

Apart from the bacteriological principle that is applicable to cell free medium from *Str. faecium* culture, it can be said that the preservation effect when treating the press fodder with a culture of *Str. faceium* will be reached partly by a quick production of lactic acid and partly through the direct or indirect bacteriostatical effect of some metabolite produced by *Str. Faecium*.

For a description of *Str. faecium*, a reference is made to the following literature:

Barnes M.E. "Journal of Applied Bacteriology", Vol. 27 (3) 1964, 461 and Whittenbury R: "The Journal of General Microbiology", 38 (1965), 279.

The conditions for growth of *Str. faecium* in green fodder a culture of *Str. Faecium* to such an extent that an initial concentration of bacterias of at least about 15,000

1. Supply of essential growth factors such as vitamins and micro-elements and some suitable nitrogen source.
2. Carbohydrates degradable by fermentation.
3. Suitable temperature.
4. Suitable moisture.

During the treatment, there is supplied to the green fodder a culture of *Str. Faecium to such an extent that an initial concentration of bacterias of at least about* 15,000 living cells per gram fodder is reached. The bacterias produce lactic acid by using available carbohydrates which are broken down in the cell sap. The relationship between carbohydrates and produced lactic acid is theoretically 1:1, i.e., from 1 gram carbohydrates, 1 gram lactic acid can be produced. In practice, this ratio is approximately 1:0.8, i.e. an exchange of lactic acid which is approximately 20% below the theoretical.

The grades of essential nutritive substances are, in general, sufficient for a satisfactory growth of bacterias which produce lactic acid. These are mostly mineral substances and nitrogenous compounds that can be used as a nitrogen source. These substances can be recovered in the cell sap, as well as some vitamins which are also necessary for the growth. The condition for utilization of these substances are, however, that the substances dissolved in the cell sap are pressed out so that a liquid medium is received.

To be able to reach an acceptable preservation effect, the final grade of lacetic acid in the pressed fodder must be at least 2%. The pH value for the ensilage containing approximately 2.5% lactic acid is about 3.5–3.8. This acidity is commonly enough for preventing non-desirable types of bacteria fermentation. The total grade of the sugar types to be broken down should consequently be at least 2.5%. In general, this demand is well satisfied.

The fermentation proceeds as the pressed fodder is kept at a suitable temperature, i.e. at least 15° C. and not exceeding 38° C. Since the lactic acid production by fermentation with *Str. faecium* is an exothermic process, maintaining a suitable fermentation temperature does not prove to be any problem. According to experience, a higher fermentation temperature will also support the growth of proteolytical organisms when fermented with, e.g., Lactobacillus, as the production of lactic acid is a slow process. When fermented with *Str. faeciu*, the production of lactic acid occurs very quickly. It is true that the temperature of the pressed fodder is raised faster than in the former case, but this does not involve any inconvenience since, at the same time, lactic acid is created to such an extent that non-desirable fermentations are effectively inhibited. At temperatures exceeding 30° C., the fermentation process is ready after 8–5 hours.

The process according to the present invention will in the following be illustrated by a non-limiting example.

EXAMPLE 100 kos green fodder (beet tops or similar) are sprayed with a bacteria suspension, the volume of which is 5–15 liters according to the water grade of the fodder. The suspension is made by dissolving a preparation containing a freeze dried culture of *Str. faecium*, carbohydrates, vitamins, riboflavine, pantotenate, folic acid, niacine and whey powder.

The quantity of living cells of *Str. faecium* in the bacteria suspension is adjusted such that approximately $20 \times 10^3$ cells per gram fodder is received. The fodder is thereafter exposed to pressure in order to press out the cell. sap. The temperature should be at least 15° C., suitably at least 18° C. Under these circumstances, the fermentation is completed and the lactic acid concentration has reached its maximum value after 3–8 days.

Although the process according to the invention has now been illustrated with references to *Streptococcus* (*Str.*) faecium, those skilled in the art will realize that any bacteria organism producing lactic acid belonging to Streptococcus and having the same qualities can be used with the same satisfactory result.

What is claimed is:

1. A process of fermentation of green fodder, wherein the green fodder is compressed to a press fodder comprising supplying to the green fodder a culture of Streptococcus faecium producing a metabiolite having anti-*E-coli*-activity, and effecting the fermentation in the presence of a nitrogen source, a source of fermentable carbohydrates and essential growth factors at a temperature of at least 15° C. until the final amount of lactic acid in the press fodder is at least 2%.

2. A process according to claim 1, wherein the fermentation is continued until a pH value of 3.5–3.8 is achieved.

3. A process according to claim 1, wherein such a quantity of the culture is supplied to the green fodder that an initial concentration of at least 15,000 living cells per gram fodder is obtained.

4. A process according to claim 3, wherein the fermentation is continued until a pH value of 3.5–3.8 is achieved.

5. A process according to claim 4, wherein said temperature is at least 18° C.

6. A process according to claim 5, wherein said initial concentration is approximately $20 \times 10^3$ cells per gram.

* * * * *